(12) United States Patent
De Kock et al.

(10) Patent No.: US 8,202,887 B2
(45) Date of Patent: Jun. 19, 2012

(54) 2-(SUBSTITUTED-AMINO)-BENZOTHIAZOLE SULFONAMIDE HIV PROTEASE INHIBITORS

(75) Inventors: Herman De Kock, Arendonk (BE); Tim Hugo Maria Jonckers, Edegem (BE); Paul Jozef Gabriel Maria Boonants, Mechelen (BE); Stefaan Julien Last, Lint (BE); Inge Dierynck, Berchem (BE); Judith Eva Baumeister, Mechelen (BE); Gerben Albert Van 'T Klooster, Breda (NL)

(73) Assignee: Janssen R&D Ireland, Little Island (IE)

( * ) Notice: Subject to any disclaimer, the term of this patent is extended or adjusted under 35 U.S.C. 154(b) by 324 days.

(21) Appl. No.: 12/304,990

(22) PCT Filed: Jun. 22, 2007

(86) PCT No.: PCT/EP2007/056235
§ 371 (c)(1),
(2), (4) Date: Dec. 15, 2008

(87) PCT Pub. No.: WO2007/147884
PCT Pub. Date: Dec. 27, 2007

(65) Prior Publication Data
US 2009/0209583 A1 Aug. 20, 2009

(30) Foreign Application Priority Data
Jun. 23, 2006 (EP) .................................. 06116003

(51) Int. Cl.
A61K 31/445 (2006.01)
A61K 31/425 (2006.01)
C07D 277/82 (2006.01)
C07D 277/60 (2006.01)
C07D 261/20 (2006.01)

(52) U.S. Cl. ........ 514/321; 514/315; 514/367; 546/198; 548/161; 548/152

(58) Field of Classification Search ................. 514/321, 514/315, 367; 546/198; 548/152, 161
See application file for complete search history.

(56) References Cited

U.S. PATENT DOCUMENTS
2004/0116485 A1* 6/2004 Surleraux et al. ............. 514/367

FOREIGN PATENT DOCUMENTS
WO 02/083657 A2 10/2002
WO 03/049746 A2 6/2003

OTHER PUBLICATIONS

Augustijns, P., et al. "Drug Absorption Studies of Prodrug Esters using the Caco-2 Model: Evaluation of Ester Hydrolysis and Transepithelial Transport", International Journal of Pharmaceutics, vol. 166 (1998) pp. 45-53.
Chou and Talalay, "Quantitative Analysis of dose-Effect Relationships: The Combined Effects of Multiple Drugs or Enzyme Inhibitors", Advanced Enzyme Regulations, vol. 22 (1984) pp. 27-55.

(Continued)

Primary Examiner — Shengjun Wang

(57) ABSTRACT

The present invention relates to 2-(substituted-amino)-benzothiazole sulfonamide compounds and derivatives, their use as protease inhibitors, in particular as broad-spectrum HIV protease inhibitors, processes for their preparation as well as pharmaceutical compositions and diagnostic kits comprising them. The present invention also concerns combinations of the present 2-(substituted-amino)-benzothiazole sulfonamide compounds and derivatives with another anti-retroviral agent. It further relates to their use in assays as reference compounds or as reagents.

10 Claims, 1 Drawing Sheet

OTHER PUBLICATIONS

Hertogs, K., et al. "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs", Antimicrobial Agents and Chemotherapy, vol. 42, No. 2 (1998) pp. 269-276.
Goodman and Gilman, "The Pharmacological Basis of therapeutics", Eighth Edition, Chapter 11, (1990) "Biotransformation of Drugs", pp. 13-15.
Surleraux, D., "Design of HIV-1 Protease Inhibitors Active on Multidrug- Resistant Virus", Journal of Medicinal Chemistry, vol. 48, No. 6, (2005), pp. 1965-1973.
Cross, L.C., et al., "Rules for the Nomenclature of Organic Chemistry Section E: Stereochemistry", Pure and Applied Chemistry, vol. 45, (1976), pp. 11-30.
International Search report for Application No. PCT/EP2007/056235 mailed Aug. 27, 2007.

* cited by examiner

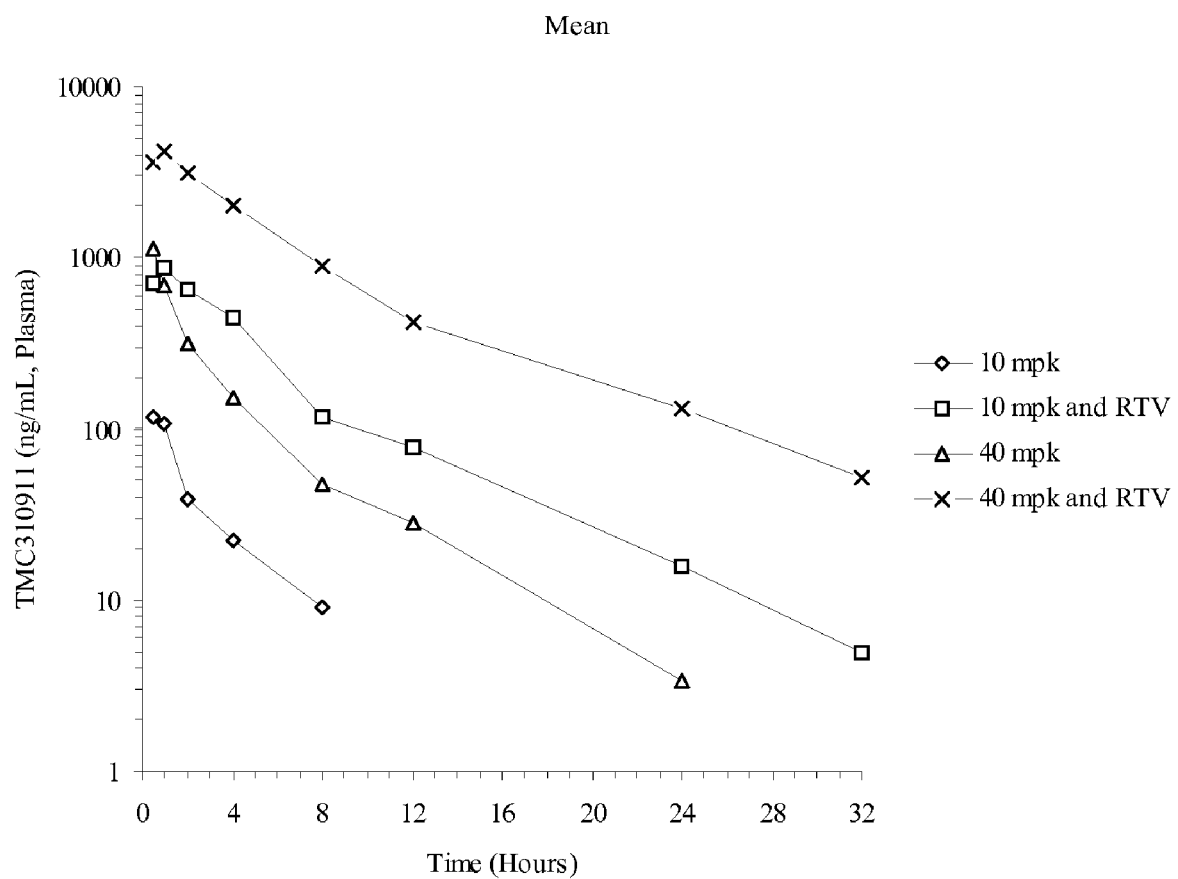

2-(SUBSTITUTED-AMINO)-BENZOTHIAZOLE SULFONAMIDE HIV PROTEASE INHIBITORS

CROSS REFERENCE TO RELATED APPLICATIONS

This application is the national stage of PCT Application No. PCT/EP2007/056235, filed Jun. 22, 2007, which claims priority from European Patent Application No. 06116003.2, filed Jun. 23, 2006, the entire disclosures of which are hereby incorporated in their entirely.

The present invention relates to 2-(substituted-amino)-benzothiazole sulfonamide compounds and derivatives, their use as protease inhibitors, in particular as broad-spectrum HIV protease inhibitors, processes for their preparation as well as pharmaceutical compositions and diagnostic kits comprising them. The present invention also concerns combinations of the present 2-(substituted-amino)-benzothiazole sulfonamide compounds and derivatives with another antiretroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by aspartic protease. For instance the HIV viral gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), fusion inhibitors such as T-20 or other protease inhibitors. Despite the fact that these antiretrovirals are very useful, they have a common limitation, namely, the targeted enzymes in HIV are able to mutate in such a way that the known drugs become less effective, or even ineffective against these mutant HIV viruses. Or, in other words HIV creates an ever-increasing resistance against the available drugs.

Resistance of retroviruses, and in particular HIV, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type HIV, but also on the increasingly more common resistant HIV.

Known antiretrovirals, often administered in a combination therapy regimen, will eventually cause resistance as stated above. This often may force the physician to boost the plasma levels of the active drugs in order for said antiretrovirals to regain effectivity against the mutated HIV. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One way of reducing this pill burden is finding anti-HIV compounds with good bioavailability, i.e. a favorable pharmacokinetic and metabolic profile, such that the daily dose can be minimized and consequently also the number of pills to be taken.

Another important characteristic of a good anti-HIV compound is that plasma protein binding of the inhibitor has minimal or even no effect on its potency.

Hitherto several protease inhibitors are on the market or are being developed.

Although the protease inhibitors on the market have excellent properties there is a constant high medical need for novel protease inhibitors that are able to combat a broad spectrum of mutants of HIV with little variance in fold resistance, have a good bioavailability, i.e. a favorable pharmacokinetic and metabolic profile, and experience little or no effect on their potency due to plasma protein binding and in addition show as little as possible side effects in human beings.

Surprisingly, the 2-(substituted-amino)-benzothiazole sulfonamide compounds and derivatives of the present invention are found to have a favorable pharmacological and pharmacokinetic profile.

Furthermore they are active against wild-type HIV but they also show a broad-spectrum activity against various mutant HIV exhibiting resistances against known protease inhibitors.

The compounds according to the invention do not induce so-called hypersensitivity reactions like skin disorders e.g. erythema and/or edema.

The present invention concerns 2-(substituted-amino)-benzothiazole sulfonamide compounds and derivatives as protease inhibitors having the formula (I)

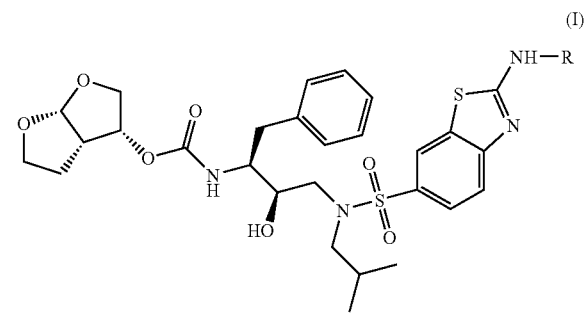

the salts, stereoisomeric forms and stereoisomeric mixtures thereof wherein

R is a piperidine or a pyrrolidine ring which is optionally substituted on one or more of the ring members by $C_{1-6}$ alkyl, $C_{3-7}$ cycloalkyl, $C_{1-6}$ alkyl-oxy-$C_{1-6}$ alkyl, —C(=O)—$C_{1-6}$ alkyl-amino-$C_{1-6}$ alkyl, —C(=O)—$C_{1-6}$alkyl-$Het^1$, —C(=O)—$C_{1-6}$alkyl-$Het^2$, benzyl, phenyl, or $C_{1-6}$ alkyl substituted by $Het^2$ wherein $Het^1$ as a group or part of a group is defined as a saturated or partially unsaturated monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl, $C_{1-6}$alkyloxy, amino$C_{1-6}$alkyl, halogen, hydroxy, acetyl, oxo, optionally mono- or disubstituted amino, optionally mono- or disubstituted aminoalkyl, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic cycle or heterocycle having 3 to 14 ring members; and wherein $Het^2$ as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl which may optionally substituted by $C_{3-7}$cycloalkyl, $C_{1-6}$alkyloxy, amino$C_{1-6}$alkyl, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, $Het^1$ and an aromatic monocyclic, bicyclic or tricyclic cycle or heterocycle having 3 to 12 ring members.

Interested compounds according to the invention are those compounds wherein R is a piperidine ring substituted on the N-atom in the ring by $C_{3-7}$ cycloalkyl.

Preferred compounds are those wherein said $C_{3-7}$ cycloalkyl is $C_5$-cylcoalkyl.

Most preferred is the compound having the formula (II)

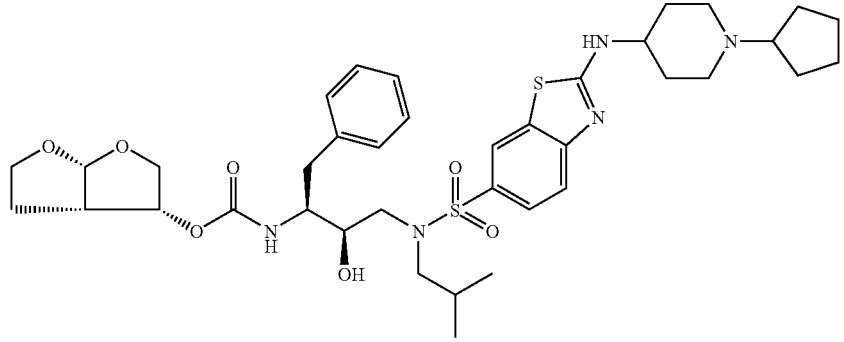

Furthermore the present invention relates to a pharmaceutical composition, and a method of preparing said pharmaceutical composition, comprising an effective amount of at least one of the compounds of formula (I) or (II) in addition to customary a pharmaceutically tolerable excipients and auxiliaries.

The pharmaceutical preparations normally contain 0.1 to 90% by weight of a compound of formula (I or II). The pharmaceutical preparations can be prepared in a manner known per se to one of skill in the art. For this purpose, at least one of a compound of formula (I or II), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals, which contain a compound according to the invention, can be administered orally using e.g. including suspensions, capsules, tablets, sachets, solutions, suspensions, emulsions; parenterally using e.g. subcutaneous, intravenous, intramuscular, intrasternal injection or infusion techniques; rectally using e.g. suppositories; intravaginally; by inhalation, or topically. The preferred administration being dependent on the individual case e.g., the particular course of the disorder to be treated. Oral administration is preferred.

The person skilled in the art is familiar on the basis of his expert knowledge with the auxiliaries, which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) or (II) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I or II) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

Due to their favorable pharmacological properties, particularly their activity against multi-drug resistant HIV protease enzymes, the compounds of the present invention are useful in the treatment of individuals infected by HIV and for the prophylaxis of these individuals.

The prophylaxis treatment can be advantageous in cases where an individual has been subjected to a high risk of exposure to a virus, as can occur when individual has been in contact with an infected individual where there is a high risk of viral transmission. As an example, prophylactic administration of said compounds would be advantageous in a situation where a health care worker has been exposed to blood from an HIV-infected individual, or in other situations where an individual engaged in high-risk activities that potentially expose that individual to HIV.

In general, the compounds of the present invention may be useful in the treatment of warm-blooded animals infected with viruses whose existence is mediated by, or depends upon, the protease enzyme. Conditions which may be prevented or treated with the compounds of the present invention include, but is not limited to, treating a wide range of states of HIV infection: AIDS, ARC (Aids related complex), both symptomatic and asymptomatic, and actual or potential exposure to HIV. The compounds of this invention are useful in treating infection by HIV after suspected past exposure to HIV by e.g., blood transfusion, exchange of body fluids, bites, accidental needle stick, or exposure to patient blood during surgery. The term prevention includes prophylaxis of HIV infection and prophylaxis of the evolution of HIV infection to AIDS.

The compounds of the present invention or any derivative thereof may therefore be used as medicines against abovementioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

The combination of an antiretroviral compound and a compound of the present invention can be used as a medicine. Thus, the present invention also relates to a product or composition containing (a) a compound of the present invention (according to formula (I or II)), and (b) another antiretroviral compound, as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, fusion inhibitors, co-receptor binding inhibitors, RT inhibitors, nucleoside RTIs, nucleotide RTIs, NNRTIs, RNAse H inhibitors, TAT inhibitors, integrase inhibitors, protease inhibitors, or glycosylation inhibitors.

The compounds of the present invention may also be administered in combination with modulators of the metabolization following application of the drug to an individual. These modulators include compounds that interfere with the metabolization at cyto-chromes, such as cytochrome P450. Some modulators inhibit cytochrome P450. It is known that several isoenzymes exist of cytochrome P450, one of which is cytochrome P450 3A4. Ritonavir is an example of a modulator of metabolization via cytochrome P450. Interesting compounds having an effect at cytochrome P450 include those compounds containing a thiazolyl, imidazolyl or pyridinyl moiety. Such combination therapy in different formulations may be administered simultaneously, separately or sequentially. Alternatively, such combination may be administered as a single formulation, whereby the active ingredients are released from the formulation simultaneously or separately.

Such modulator may be administered at the same or different ratio as the compound of the present invention. Preferably, the weight ratio of such modulator vis-à-vis the compound of the present invention (modulator: compound of the present invention) is 1:1 or lower, more preferable the ratio is 1:3 or lower, suitably the ratio is 1:10 or lower, more suitably the ratio is 1:30 or lower.

The combination may provide a synergistic effect, whereby viral infectivity and its associated symptoms may be prevented, substantially reduced, or eliminated completely. Combinations of the compounds of formula (I or II) with another HIV protease inhibitor, or a so-called booster such as Ritonavir, as cytochrome $P_{450}$ inhibitor can act synergistically, in an additive way or antagonistically. This can be assessed in an experimental setting where the potency of different ratios of the two HIV-protease inhibitors is measured. Results can be plotted in an isobologram graph according to the method described by Chou and Talalay (Adv. Enzyme Regul. 22: 27-55, 1984) Synergism between two inhibitors would mean a more potent combination therapy, but with no increase in undesired side effects.

Part of the invention is the use of ritonavir or a pharmaceutically acceptable salt thereof in the manufacture of a medicament for the inhibition or treatment of an HIV infection or AIDS in a human in combination with compounds I or II, preferably compound II, which is metabolized by cytochrome P450 wherein the amount of ritonavir is sufficient to improve the pharmacokinetics of said compounds I or II in a patient, relative to the pharmacokinetics of the respective compounds I or II when administered alone.

Another aspect of the present invention concerns a kit or container comprising a compound of formula (I or II) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in phenotypic resistance monitoring assays, such as known recombinant virus assays, in the clinical management of resistance developing diseases such as HIV. A particularly useful resistance monitoring system is a recombinant virus assay known as the Antivirogram™. The Antivirogram™ is a highly automated, high throughput, second generation, recombinant virus assay that can measure susceptibility, especially viral susceptibility, to the compounds of the present invention. (Hertogs K, de Bethune M P, Miller V et al. *Antimicrob Agents Chemother,* 1998; 42(2):269-276)

Whenever the term "substituted" is used in defining the compounds of formula (I or II), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "$C_{1-6}$alkyl" as a group or part of a group defines straight and branched chained saturated hydrocarbon radicals having from 1 to 6 carbon atoms such as methyl, ethyl, propyl, butyl, 2-methyl-propyl, pentyl, hexyl, 2-methylbutyl, 3-methylpentyl and the like.

The term "$C_{3-7}$cycloalkyl" as a group or part of a group is generic to cyclopropyl, cyclobutyl, cyclopentyl, cyclohexyl or cycloheptyl.

As used herein, the term (=O) forms a carbonyl moiety with the carbon atom to which it is attached.

When any variable (e.g. halogen or $C_{1-4}$alkyl) occurs more than one time in any constituent, each definition is independent.

Het$^1$ as a group or part of a group is defined as a saturated or partially unsaturated monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl, $C_{1-6}$alkyloxy, amino$C_{1-6}$alkyl, halogen, hydroxy, acetyl, oxo, optionally mono- or disubstituted amino, optionally mono- or disubstituted aminoalkyl, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic cycle or heterocycle having 3 to 14 ring members.

Het$^2$ as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl which may optionally substituted by $C_{3-7}$cycloalkyl, $C_{1-6}$alkyloxy, amino$C_{1-6}$alkyl, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, Het$^1$ and an aromatic monocyclic, bicyclic or tricyclic cycle or heterocycle having 3 to 12 ring members.

The term "aryl" refers to any functional group or substituent derived from a simple aromatic ring. There are more specific terms, such as phenyl, to describe unsubstituted aryl groups and subsets of aryl groups (as well as arbitrarily substituted groups), but "aryl" is used for the sake of abbreviation or generalization.

For therapeutic use, the salts of compounds of formula (I) or (II) are those wherein the counter ion is pharmaceutically or physiologically acceptable. However, salts having a pharmaceutically unacceptable counter ion may also find use, for example, in the preparation or purification of a pharmaceutically acceptable compound of formula (I) or (II). All salts, whether pharmaceutically acceptable or not are included within the ambit of the present invention.

The pharmaceutically acceptable or physiologically tolerable addition salt forms, which the compounds used in the present invention are able to form, can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) or (II) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like.

The present compounds used in the present invention may also exist in their N-oxide forms of formula (I) or (II) wherein one or several nitrogen atoms are oxidized to the so-called N-oxide. To obtain said N-oxides the compounds of formula (I or II) may be converted to the corresponding N-oxide forms following art-known procedures for converting a trivalent nitrogen into its N-oxide form. Said N-oxidation reaction may generally be carried out by reacting the starting material of formula (I or II) with appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "compound or compounds having the formula (I) or (II)", or any similar terms such as "compound or compounds of the invention" and the like, is meant to also comprise any prodrugs that the compounds of formula (I) or (II) may form. The term "prodrug" as used herein is meant to comprise any pharmacologically acceptable derivatives such as esters, amides and phosphates, such that the resulting in vivo biotransformation product of the derivative is the active drug as defined in the compounds of formula (I) or (II). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) or (II) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxy-methyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyl-oxyethyl; 1,3-dioxolen-2-onylmethyl esters for example 5-methyl-1,3-dioxolen-2-only-methyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) or (II) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring. Alkanoyl esters for example are any $C_{1-30}$alkanoyl esters, in particular $C_{8-30}$alkanoyl esters, and more in particular $C_{10-24}$alkanoyl esters, further in particular $C_{16-20}$alkanoyl esters, wherein the alkyl part may have one or more double bonds. Examples of alkanoyl esters are decanoate, palmitate and stearate.

The term "compound or compounds having the formula (I) or (II)", or any similar terms such as "compound or compounds of the invention" and the like, is meant to also comprise any metabolites that are formed in vivo upon administration of the drug. Some examples of metabolites in accordance with the invention include, but are not limited to, (a) where the compound of formula (I) or (II) contains a methyl group, a hydroxymethyl derivative thereof, (b) where the compound of formula (I) or (II) contains an alkoxy group, an hydroxy derivative thereof, (c) where the compound of formula (I) or (II) contains a tertiary amino group, a secondary amino derivative thereof, (d) where the compound of formula (I) or (II) contains a secondary amino group, a primary derivative thereof, (e) where the compound of formula (I) or (II) contains a phenyl moiety, a phenol derivative thereof, and (f) where the compound of formula (I) or (II) contains an amide group, a carboxylic acid derivative thereof.

The present invention is also intended to include any isotopes of atoms present in the compounds of the invention. For example, isotopes of hydrogen include tritium and deuterium and isotopes of carbon include C-13 and C-14.

The present compounds used in the invention may also exist in their tautomeric forms. Such forms, although not explicitly indicated in the above formula are intended to be included within the scope of the present invention.

The present compound used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereo specifically. Preferably, if a specific stereoisomer is desired, said compound will be synthesized by stereospecific methods of preparation. These methods will advantageously employ enantiomerically pure starting materials.

The diastereomeric racemates of formula (I or II) can be obtained separately by conventional methods. Appropriate physical separation methods, which may advantageously be employed, are for example selective crystallization and chromatography, e.g. column chromatography.

It is clear to a person skilled in the art that compounds of formula (I) or (II) contains five asymmetric centers and thus may exist as different stereoisomeric forms. Two asymmetric centers are indicated with an asterisk (*) in the FIGURE below for formula (I)

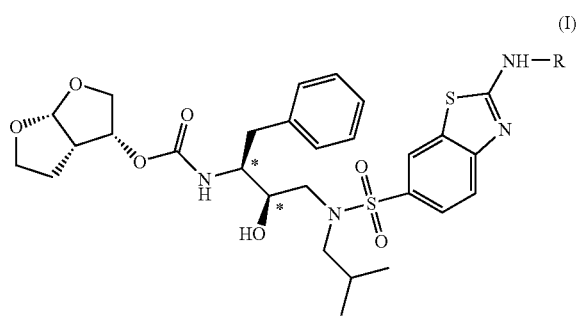

(I)

The absolute configuration of each asymmetric center that may be present in the compounds of formula (I) may be indicated by the stereochemical descriptors R and S, this R and S notation corresponding to the rules described in Pure Appl. Chem. 1976, 45, 11-30.

The same is applicable to formula (II).

BRIEF DESCRIPTION OF DRAWING

FIG. 1 represents the mean plasma concentration time plots for compound II with and without co-administration of ritonavir.

EXAMPLE SECTION

General Experimental Procedures

NMR spectra were recorded on a Bruker Avance 400 spectrometer, operating at 400 MHz for $^1$H with CDCl$_3$ as solvent. In every case tetramethylsilane (TMS) was used as internal standard. Chemical shifts are given in ppm and J values in Hz. Multiplicity is indicated using the following abbreviations: d for doublet, t for a triplet, m for a multiplet, etc. For the sake of brevity it was opted to completely characterize (NMR included) one representative example of each subset of compounds. Low-resolution mass spectra (LRMS) were performed on an ion trap (ThermoFinnigan LCQ Deca) or a time of flight (Waters LCT) mass spectrometer using electrospray ionization (ESI) in positive mode. All reagents, were purchased from commercial sources (Acros, Aldrich, Fluorochem, . . . ) and were used as received. Column chromatography was carried out on silica gel 60 Å, 60-200 μm (ROCC). Thin layer chromatography was performed on silica gel 60 F$_{254}$ plates (Merck). Analytical HPLC was done on a Waters Alliance 2795 (pump+auto sampler) system equipped with a Waters 996 photo diode array-detector (system 1 and system 2). To check the purity of the end products two chromatographic systems were used. System 1: column: Waters Xterra MS C18, (3.5 μm, 4.60 mm×100 mm), mobile phase A: 20 mM CH$_3$COONH$_4$ and 5% CH$_3$CN in H$_2$O, mobile phase B: CH$_3$CN. Analysis were run at 55° C. using a flow rate of 1.5 mL/min applying the following gradient: 0 min: 95% A, 5.4 min: 5% A, 7.2 min: 5% A. In every case, 10 μl of a 1 mM solution was injected. The equilibration time between two runs was 1.8 minutes. Eluted peaks were detected at a single wavelength ($\lambda_{max}$). System 2: column: Waters SunFire C18, (3.5 μm, 4.60 mm×100 mm), mobile phase A: 10 mM HCOONH$_4$ and 0.1% HCOOH in H$_2$O, mobile phase B: CH$_3$CN. Analysis were run at 55° C. using a flow rate of 1.5 mL/min applying the following gradient: 0 min: 95% A, 5.4 min: 5% A, 7.2 min: 5% A. Eluted peaks were detected at a single wavelength ($\lambda_{max}$). The retention time for one representative example of each subset of compounds is given and is reported in minutes. The synthesis of one representative example (compound 7 in class A) is fully described. The other compounds (in class A and B, C and D respectively) were synthesized in the same way as already described.

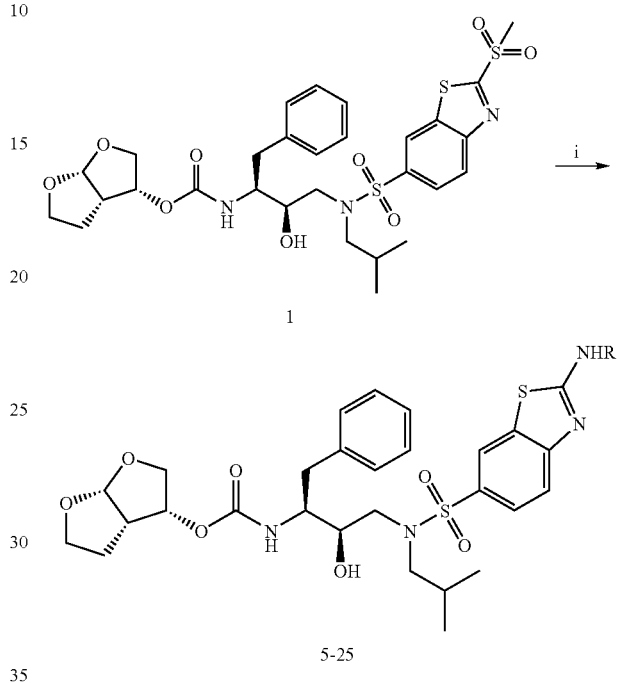

Scheme 1. Synthesis of {1-Benzyl-3-[(2-amino-benzothiazole-6-sulfonyl)-isobutyl-amino]-2-hydroxy-propyl}-carbamic acid hexahydro-furo[2,3-b]furan-3-yl ester derivatives 5-25.

(i) RNH$_3$$^+$Cl$^-$/Et$_3$N, THF/10% Na$_2$CO$_3$.

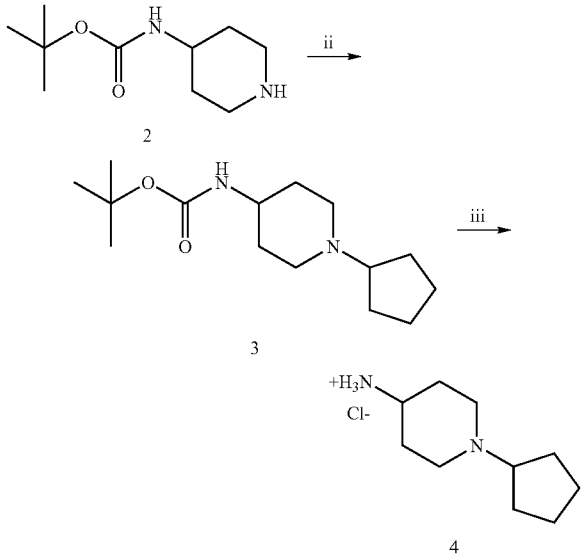

Scheme 2. Synthesis of 1-cyclopentyl-piperidin-4-yl-ammonium chloride (4).

(ii) Iodo-cyclopentane, K$_2$CO$_3$, CH$_3$CN; (iii) HCl/i-PrOH, CH$_3$OH.

Example 1

Description of the Chemical Reactions for Scheme 2

(1-Cyclopentyl-piperidin-4-yl)-carbamic acid tert-butyl ester (3)

This compound was synthesized from the commercially available piperidin-4-yl-carbamic acid tert-butyl ester (2) (5 g, 25 mmol, 1 equiv) which was dissolved in acetonitrile (150 mL), followed by the addition of iodo-cyclopentane (9.79 g, 50 mmol, 2 equiv) and $K_2CO_3$ (3.45 g, 25 mmol, 1 equiv). The solution was stirred at room temperature for 48 hours. Due to the incompleteness of the reaction, iodocyclo-pentane (1.70 g, 8.69 mmol, 0.35 equiv) and $K_2CO_3$ (1 g, 7.25 mmol, 0.29 equiv) were added to the solution. The solution was stirred at room temperature for several hours. The solution was filtered over a bed of dicalite and the filtrate was evaporated under reduced pressure to obtain 3 (6.70 g, 25 mmol, quantitative). LRMS (ES+): m/z 269.

1-Cyclopentyl-piperidin-4-yl-ammonium chloride (4)

(1-Cyclopentyl-piperidin-4-yl)-carbamic acid tert-butyl ester (3) (6.70 g, 25 mmol, 1 equiv) was dissolved in methanol (30 mL), followed by the addition of 6 N HCl in isopropanol (10 mL). The solution was stirred at room temperature for 24 hours. Due to the incompleteness of the reaction, 6 N HCl in isopropanol (10 mL) and methanol (50 mL) were added to the solution. The solution was stirred at room temperature for another 24 hours. LC-MS indicated incompletion of the reaction. Tetrahydrofurane (20 mL), 6 N HCl in isopropanol (10 mL) and methanol (200 mL) were added to the solution. The solution was stirred at room temperature for 5 hours, followed by the addition of 6 N HCl in isopropanol (10 mL). The solution was stirred at room temperature for 72 hours. The solution was evaporated under reduced pressure to obtain 4 (4.20 g, 25 mmol, quantitative). LRMS (ES+): m/z 169.

Example 2

Description of the Chemical Reactions for Scheme 1

Preparation of compound (1-benzyl-3-{[2-(1-cyclopentyl-piperidin-4-ylamino)-benzothiazole-6-sulfonyl]-isobutyl-amino}-2-hydroxy-propyl)-carbamic acid hexahydro-furo[2,3-b]furan-3-yl ester (7) (class A)

{1-Benzyl-2-hydroxy-3-[isobutyl-(2-methanesulfonyl-benzothiazole-6-sulfonyl)-amino]-propyl}-carbamic acid hexahydro-furo[2,3-b]furan-3-yl ester (1)[1,2] (10 g, 15 mmol, 1 equiv), 1-cyclopentyl-piperidin-4-yl-ammonium chloride (4) (6.02 g, 25 mmol, 1.67 equiv) and triethylamine (6.10 g, 60 mmol, 4 equiv) were dissolved in tetrahydrofurane (200 mL), followed by the addition of 10% $Na_2CO_3$ in water (50 mL). The solution was stirred at room temperature for 48 hours. The organic layer was separated and washed with saturated $NaHCO_3$ solution. The organic layer was dried on $MgSO_4$, filtered and evaporated under reduced pressure. The crude product was purified by column chromatography on elution with dichloromethane:ammonia in methanol (7N) (100 to 95:5) to yield the title compound (4.45 g, 15 mmol, 39%). LRMS (ES+): m/z 756 [M+H]$^+$; HPLC (system 1) (290 nm) $t_R$ 4.16 min, 97.11%; $^1$H-NMR (CDCl$_3$) 0.87 (d, 3H, J=6.48, CH$_3$), 0.92 (d, 3H, J=6.50, CH$_3$), 1.33-1.51 (m, 4H, CH$_2$ (2×) (cyclopentyl)), 1.51-1.77 (m, 6H, CH$_2$ (2×) (piperidine) and CH$_2$, H4), 1.77-1.96 (m, 5H, CH$_2$ (2×) (cyclopentyl) and CH (isobutyl)), 2.09-2.28 (m, 4H, CH$_2$ (2×) (piperidine)), 2.43-2.59 (m, 1H, CH (cyclopentyl)), 2.72-2.85 (m, 1H, OH), 2.85-2.92 (m, 1H, CH, H3a), 2.92-3.12 (m, 5H, CH (piperidine) and CH$_2$—N and CH$_2$ (isobutyl)), 3.20 (dd, 2H, J=8.63 and J=15.16, CH$_2$ of C$_6$H$_5$CH$_2$), 3.58-3.79 (m, 3H, CH$_2$, H5 and CH$_2$, H2), 3.79-3.91 (m, 3H, CH$_2$, H2 and CH—NH and CH—OH), 4.90-5.10 (m, 2H, CH, H3 and NH), 5.42-5.59 (m, 1H, NH), 5.62 (d, 1H, J=5.04, CH, H6a), 7.12-7.32 (m, 5H, C$_6$H$_5$), 7.52 (d, 1H, J=8.54, CH (benzthiazole)), 7.67 (dd, 1H, J=0.99 and J=8.47, CH (benzthiazole)), 7.95-8.02 (brs, 1H, CH (benzthiazole)).

---

[1] Surleraux, D. L. N. G. et al. Broad spectrum 2-(substituted-amino)-benzothiazolesulfonamide HIV protease inhibitors/PCT Int. Apl. 2002, WO2002083657.

[2] Surleraux, D. L. N. G. et al. Design of HIV-1 Protease Inhibitors Active on Multidrug-Resistant Virus.; *J. Med. Chem.* 2005, 48, 1965-1973.

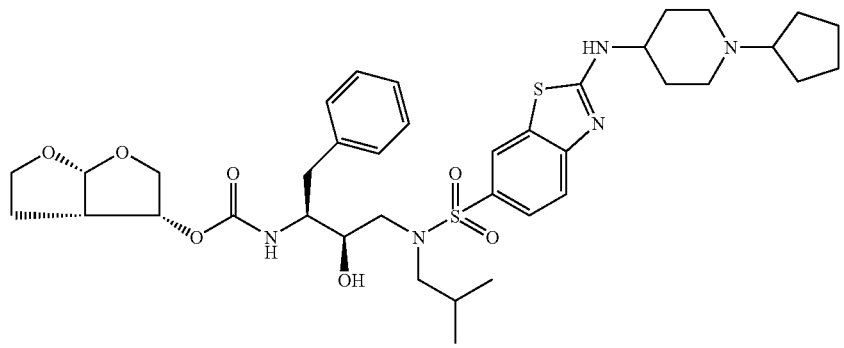

Preparation of compound (1-Benzyl-3-{[2-(1-benzyl-piperidin-4-ylamino)-benzothiazole-6-sulfonyl]-isobutyl-amino}-2-hydroxy-propyl)-carbamic acid hexahydro-furo[2,3-b]furan-3-yl ester (11) (class B)

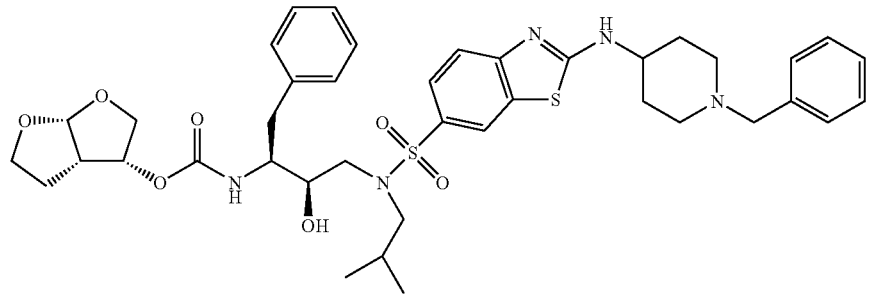

LRMS (ES+): m/z 778 [M+H]⁺; HPLC (system1) (296 nm) $t_R$ 4.92 min, 95.51%; HPLC (system 2) (296 nm) $t_R$ 3.65 min, 95.41%; ¹H-NMR (CDCl₃) δ0.90 (d, 3H, J=6.52, CH₃), 0.97 (d, 3H, J=6.55, CH₃), 1.55-1.71 (m, 6H, CH₂ (2×) (piperidine) and CH₂, H4), 1.71-1.99 (m, 1H, CH (isobutyl)), 2.09-2.19 (m, 2H, CH₂ (piperidine)), 2.19-2.35 (m, 2H, CH₂ (piperidine)), 2.70-2.93 (m, 3H, CH (piperidine) and CH, H3a and OH), 2.93-3.12 (m, 4H, CH₂—N and CH₂ (isobutyl)), 3.12-3.29 (m, 2H, CH₂ of C₆H₅CH₂), 3.58 (s, 2H, C₆H₅CH₂), 3.61-3.81 (m, 3H, CH₂, H5 and CH₂, H2), 3.81-3.92 (m, 3H, CH₂, H2 and CH—NH and CH—OH), 4.91-5.11 (m, 2H, CH, H3 and NH), 5.49-5.61 (m, 1H, NH), 5.62 (d, 1H, J=5.15, CH, H6a), 7.08-7.41 (m, 10H, C₆H₅), 7.55 (d, 1H, J=8.55, CH (benzthiazole)), 7.67 (dd, 1H, J=1.63 and J=8.56, CH (benzthiazole)), 7.92-8.10 (m, 1H, CH (benzthiazole)).

Preparation of compound [1-Benzyl-2-hydroxy-3-(isobutyl-{2-[1-(2-methoxy-ethyl)-pyrrolidin-3-ylamino]-benzothiazole-6-sulfonyl}-amino)-propyl]-carbamic acid hexahydro-furo[2,3-b]furan-3-yl ester (17) (class C)

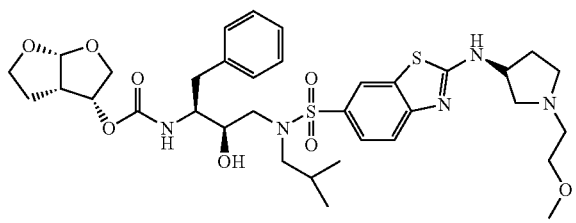

LRMS (ES+): m/z 732 [M+H]⁺; HPLC (system 1) (286 nm) $t_R$ 4.06 min, 89.02%; HPLC (system 2) (286 nm) $t_R$ 3.42 min, 87.19%; ¹H-NMR (CDCl₃) δ0.89 (d, 3H, J=6.49, CH₃), 0.95 (d, 3H, J=6.56, CH₃), 1.55-1.72 (m, 2H, CH₂, H4), 1.75-2.03 (m, 3H, CH (isobutyl) and CH₂ (pyrrolidine)), 2.31-2.50 (m, 6H, CH₂ (2×) (pyrrolidine) and CH₂), 2.75-2.87 (m, 1H, OH), 2.87-3.12 (m, 8H, CH₂—N and CH₂ (isobutyl) and CH, H3a and CH (pyrrolidine) and CH₂), 3.12-3.27 (m, 2H, CH₂ of C₆H₅CH₂), 3.38 (s, 3H, CH₃), 3.60-3.75 (m, 3H, CH₂, H5 and CH₂, H2), 3.81-4.05 (m, 3H, CH₂, H2 and CH—NH and CH—OH), 4.92-5.08 (m, 2H, CH, H3 and NH), 5.62 (d, 1H, J=5.15, CH, H6a), 6.30-6.42 (m, 1H, NH), 7.12-7.40 (m, 5H, C₆H₅), 7.57 (d, 1H, J=8.54, CH (benzthiazole)), 7.68 (dd, 1H, J=1.96 and J=6.61, CH (benzthiazole)), 8.00 (d, 1H, J=1.57, CH (benzthiazole)).

Preparation of compound (1-Benzyl-2-hydroxy-3-{isobutyl-[2-(1-pyridin-3-ylmethyl-pyrrolidin-3-ylamino)-benzothiazole-6-sulfonyl}-amino]-propyl)-carbamic acid hexahydro-furo[2,3-b]furan-3-yl ester (21) (class D)

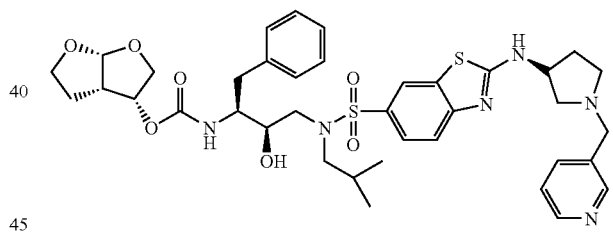

LRMS (ES+): m/z 765 [M+H]⁺; HPLC (system 1) (286 nm) $t_R$ 4.28 min, 95.18%; HPLC (system 2) (286 nm) $t_R$ 3.40 min, 94.56%; ¹H-NMR (CDCl₃) δ0.88 (d, 3H, J=6.34, CH₃), 0.90 (d, 3H, J=6.38, CH₃), 1.50-1.65 (m, 2H, CH₂, H4), 1.65-1.98 (m, 3H, CH (isobutyl) and CH₂ (pyrrolidine)), 2.20-2.52 (m, 4H, CH₂ (2×) (pyrrolidine)), 2.75-3.28 (m, 11H, CH, H3a and OH and CH₂—N and CH₂ (isobutyl) and CH (pyrrolidine) and CH₂ of C₆H₅CH₂ and CH₂), 3.55-3.75 (m, 3H, CH₂, H5 and CH₂, H2), 3.75-4.05 (m, 3H, CH₂, H2 and CH—NH and CH—OH), 4.90-5.10 (m, 2H, CH, H3 and NH), 5.65 (d, 1H, J=4.50, CH, H6a), 6.18-6.49 (m, 1H, NH), 7.12-7.40 (m, 6H, C₆H₅ and CH (pyridine)), 7.50-7.60 (m, 1H, CH (benzthiazole)), 7.60-7.75 (m, 2H, CH (benzthiazole) and CH (pyridine)), 7.91-8.08 (m, 1H, CH (benzthiazole)), 8.40-8.65 (m, 2H, CH (pyridine)).

The compounds prepared (no's. 5-25) are depicted below in Table 1 and grouped in classes A, B, C and D respectively.

TABLE 1
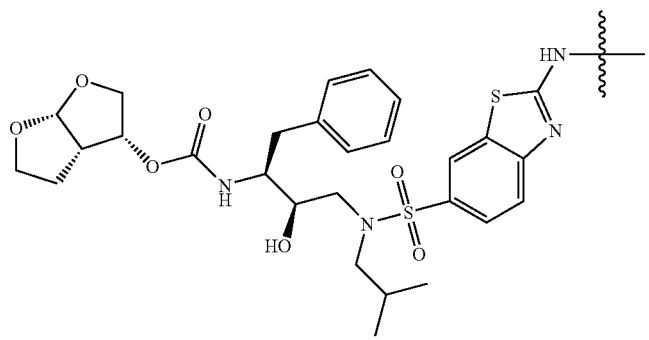
| Compound No | Class | R | MF | LC-MS ES+ |
|---|---|---|---|---|
| 5 | A | piperidine-N-isopropyl | C36H51N5O7S2 | 730 |
| 6 | A | piperidine-N-isobutyl | C37H53N5O7S2 | 744 |
| 7 | A | piperidine-N-cyclopentyl | C38H53N5O7S2 | 756 |
| 8 | A | piperidine-N-CH2CH2OCH3 | C36H51N5O8S2 | 746 |
| 9 | A | piperidine-N-C(O)CH2N(CH3)2 | C37H52N6O8S2 | 773 |
| 10 | A | piperidine-N-C(O)CH2-morpholine | C39H54N6O9S2 | 816 |
| 11 | B | piperidine-N-benzyl | C40H51N5O7S2 | 778 |
| 12 | B | piperidine-N-CH2-(4-pyridyl) | C39H50N6O7S2 | 779 |

TABLE 1-continued

| Compound No | Class | R | MF | LC-MS ES+ |
|---|---|---|---|---|
| 13 | B | (piperidine-N-CH2-pyridin-2-yl) | C39H50N6O7S2 | 779 |
| 14 | B | (piperidine-N-CH2-pyridin-3-yl) | C39H50N6O7S2 | 779 |
| 15 | B | (piperidine-N-CH2-thiazol-5-yl) | C37H48N6O7S3 | 785 |
| 16 | C | (pyrrolidin-3-yl, NH) | C32H43N5O7S2 | 674 |
| 17 | C | (pyrrolidin-3-yl, N-CH2CH2OMe) | C35H49N5O8S2 | 732 |
| 18 | C | (pyrrolidin-3-yl, N-CH2CH2OMe) | C35H49N5O8S2 | 732 |
| 19 | C | (pyrrolidin-3-yl, N-isobutyl) | C36H51N5O7S2 | 730 |
| 20 | C | (pyrrolidin-3-yl, N-isobutyl) | C36H51N5O7S2 | 730 |

TABLE 1-continued

| Compound No | Class | R | MF | LC-MS ES+ |
|---|---|---|---|---|
| 21 | D | (3-pyridylmethyl)pyrrolidin-3-yl | C38H48N6O7S2 | 765 |
| 22 | D | (4-pyridylmethyl)pyrrolidin-3-yl | C38H48N6O7S2 | 765 |
| 23 | D | (thiazol-5-ylmethyl)pyrrolidin-3-yl | C36H46N6O7S3 | 771 |
| 24 | D | (thiazol-5-ylmethyl)pyrrolidin-3-yl (epimer) | C36H46N6O7S3 | 771 |
| 25 | D | (2-pyridylmethyl)pyrrolidin-3-yl | C38H48N6O7S2 | 765 |

Example 3

Virological Properties of the Compounds of the Current Invention

The compounds were tested in a cellular assay using the MT4-LTR-EGFP cells for anti-viral activity. The assay demonstrated that these compounds exhibit potent anti-HIV activity against a wild type laboratory HIV strain (WT IIIB-2-001).

Because of the increasing emergence of drug resistant HIV strains, the present compounds were tested for their potency against clinically isolated HIV strains harboring several mutations. These mutations are associated with resistance to protease inhibitors and result in viruses that show various degrees of phenotypic cross-resistance to the currently commercially available drugs such as for instance saquinavir, ritonavir, nelfinavir, indinavir and amprenavir. The viral strains coded as A, B, C and D contain mutations as indicated below in Table 2.

TABLE 2

| | |
|---|---|
| A | V003I, L010I, V032T, L033M, E035D, S037Y, M046I, R057R/K, Q058E, L063P, K070T, A071V, I072V, I084V, L089V |
| B | V003I, V032I, L035D, M036I, S037N, K043T, M046I, I047V, I050V, K055R, I057K, I062V, L063P, A071L, V082I, I085V, L090M, I093L |
| D | V003I L010I I013V G016A/G L019I L033F S037N M046I I050V F053L I054V K055R L063P A071V G073C V077I/V V082A L090M |
| C | V003I L010F I013V V032T S037N M046I I047V I050V L063P A071V I084V L089V T091A Q092R |

The cellular assay was performed according to the following procedure. HIV- or mock-infected MT4-LTR-EGFP cells were incubated for three days in the presence of various concentrations of the compounds according to the invention. Upon infection, the viral tat protein activates the GFP reporter. At the end of the incubation period, the GFP signal was measured. In the virus control samples (in the absence of any inhibitor) the maximal fluorescent signal was obtained. The inhibitory activity of the compound was monitored on the virus-infected cells and was expressed as $EC_{50}$. These values represent the amount of the compound required to protect 50% of the cells from virus infection. (Table 3).

As can be seen in this table the present compounds are effective in inhibiting a broad range of mutant strains.

TABLE 3

| | | Virus strains | | | |
|---|---|---|---|---|---|
| Compound No | WT-IIIB-2-001 pEC50 | A pEC50 | B pEC50 | C pEC50 | D pEC50 |
| 5 | 7.72 | 7.89 | 7.57 | 5.38 | 7.86 |
| 6 | 8.31 | 7.84 | 7.58 | 5.46 | 7.86 |
| 7 | 7.88 | 7.93 | 7.70 | 5.54 | 7.87 |
| 8 | 7.44 | 6.65 | 7.00 | 5.25 | NA |
| 9 | 6.56 | 6.99 | 6.59 | 5.00 | 6.99 |
| 10 | 6.53 | 6.84 | 6.52 | 5.11 | 6.62 |
| 11 | 8.60 | 7.65 | 7.47 | 5.24 | 7.73 |
| 12 | 8.34 | 8.26 | 7.71 | 5.19 | 8.27 |
| 13 | 8.18 | 8.06 | 7.94 | 6.04 | 7.98 |
| 14 | 7.85 | 7.85 | 7.78 | 5.90 | 7.84 |
| 15 | 8.24 | 8.38 | 7.71 | 5.46 | 8.24 |
| 16 | 6.82 | 5.93 | 5.89 | 5.90 | NA |
| 17 | 7.73 | 7.88 | 7.77 | 5.47 | NA |
| 18 | 7.76 | 7.61 | 7.24 | 5.32 | NA |
| 19 | 8.42 | 7.84 | 7.33 | 5.35 | 7.75 |
| 20 | 8.27 | 8.23 | 7.84 | 5.59 | 8.12 |
| 21 | 7.95 | 8.31 | 7.84 | 5.74 | 8.15 |
| 22 | 7.71 | NA | 7.77 | 6.19 | NA |
| 23 | 7.97 | 8.56 | 7.56 | 5.36 | 8.27 |
| 24 | 8.22 | 7.91 | 7.70 | 5.08 | 7.89 |
| 25 | 5.77 | 5.59 | 5.04 | <4.49 | 5.41 |

Example 4

Bioavailability

Caco-2 Permeability Assay for Intestinal Absorption

The permeability of different compounds was evaluated according to a Caco-2 test protocol as described by Augustijns et al. (Augustijns et al. (1998). *Int. J. of Pharm*, 166, 45-54) whereby, Caco-2 cells at cell passage number between 32 and 45 were grown in 24-well cell culture plates for 21 to 25 days. The integrity of the cell monolayer was checked by measuring the transepithelial electrical resistance (TEER). The test was performed at pH 7.4 and at 100 μM donor compound concentration.

Aqueous Solubility at Different pH Levels

The equilibrium solubility in simulated gastrointestinal solutions under thermodynamic conditions is a good measure for the solubility profile of the compound in the stomach and the different parts of the intestine. Simulated gastric fluid (SGF) (without pepsin) was set at pH of 1.5. Simulated intestinal fluids (SIF) (without bile salts) were set at pH 5, pH 6.5, pH 7 and pH 7.5. The experimental protocol used 96-well flat-bottom microplates in which 1 mg of compound is added per well (stock solution in methanol) and evaporated to dryness. The compounds were resolubilized in SGF and SIF and incubated overnight on a horizontal shaking device at 37° C. After filtration, the compound concentrations were determined by UV-spectrophotometry.

Protein Binding Analyses:

Human serum proteins like albumin (HSA) or alpha-1 acid glycoprotein (AAG) are known to bind many drugs, resulting in a possible decrease in the effectiveness of those compounds. In order to determine whether the present compounds would be adversely affected by this binding, the anti-HIV activity of the compounds was measured in the presence of human serum, thus evaluating the effect of the binding of the protease inhibitors to those proteins.

Oral Availability in the Rat

The compounds were formulated as a 20 mg/ml solution or suspension in DMSO, PEG400 or cyclodextrine 40% in water. For most experiments in the rat (male and female rats), three dosing groups were formed: 1/single intraperitoneal (IP) dose at 20 mg/kg using DMSO formulation; 2/single oral dose at 20 mg/kg using PEG400 formulation and 3/single oral dose at 20 mg/kg using PEG400 formulation. Blood was sampled at regular time intervals after dosing and drug concentrations in the serum were determined using a LC-MS bioanalytical method. Serum concentrations were expressed in ng/mg. Serum concentration at 30 minutes (30') and at 3 hours (180') were determined as these values reflect the extent of absorption (30') and the speed of elimination (180').

Boosting the Systemic Bioavailability

With the described type of compounds (protease-inhibitors), it is known that inhibition of the metabolic degradation processes can markedly increase the systemic availability by reducing the first-pass metabolism in the liver and the metabolic clearance from the plasma. This 'boosting' principle can be applied in a clinical setting to the pharmacological action of the drug. This principle can be also explored both in the rat or the dog by simultaneous administration of a compound that inhibits the Cyt-P450 metabolic enzymes. Known blockers are for example ritonavir and ketoconazole. Dosing a single oral dose of ritonvir at 5 mg/kg in the rat and the dog may result in an increase of the systemic availability.

Hypersensitivity Testing of the Compounds According to the Invention

Studies were carried out to test for the occurrence of erythema and edema in dogs. The compound having structural formula (II) was orally administered to Beagle dogs in an appropriate formulation as a single-dose, dose-escalating study design. In order to achieve high systemic exposures, a so-called booster compound was co-administered (ritonavir, RTV). Blood samples were taken at regular time points following the dosing. Clinical signs were recorded at least once daily for the treatment period and follow up (for at least 24 hours). Symptoms were graded on a 1-3 scale, with 0 being absence of symptoms, 1 mild, 2, moderate, 3 severe, 4 very severe. Special attention was paid to the occurrence of erythema and edema.

The concentration of the compound having formula (II) in dog plasma was determined using a LC-MS/MS method. Raw data were used to calculate standard pharmacokinetic parameters (e.g. AUC) as a measure of systemic exposure. The systemic exposure for the compound having formula (II) was compared to the exposure of a reference compound having structural formula (III), in similar single-dose experiments in dogs, in the absence of a booster (ritonavir).

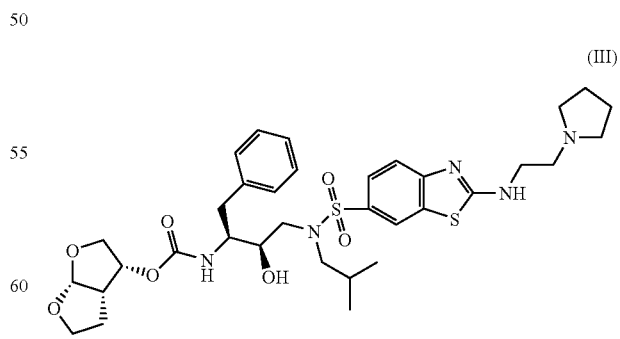

(III)

The table below provides comparative plasma exposure to the compound having formula (II) and the compound having the formula (III) in these dogs, with the associated observations on erythema and edema.

Surprisingly, it was found, that the compound having structural formula II did not induce erythema and/or edema in single dose experiments in dogs, whereas the compound having the formula (III) did induce these clinical signs.

| Compound | Dose (mg/kg) | AUC (ng · h/ml) | Erythema/edema |
|---|---|---|---|
| Compound having formula (II) + RTV* | 20 | 7747** | No |
| | 40 | 23016** | No |
| | 80 | 23016** | No |
| Reference compound having formula (III) | 10 | 47-238 | No |
| | 40 | 3319-5088 | No |
| | 80 | 7366-15998 | Yes |
| | 120 | 10204-27507 | Yes |

*RTV: coadministration of ritonavir ('booster') to increase the exposure of the compound having formula (II)
*mean AUC calculated from 4 animals Comparison of Compound III Erythema/Edema Effects to Compound II Profile Compound III:

In a single dose escalation/five day repeat dose toxicology tolerance study in beagle dog, one of two males and one of two females treated with compound III exhibited general erythema at the high dose level of 80 mg/kg/day after five consecutive days of treatment.

In a 28 day toxicology study in beagle dogs most animals treated with compound III showed slight to severe redness of the skin (erythema; general or maculate) at all dose levels. At the low dose level of 40 mg/kg/day these symptoms began to occur in the third week of the study; for dose levels of 80 and 120 mg/kg/day, these effects were present from the start of the study. In most cases the erythema was accompanied by swelling (edema) on the head, flews, eyes and/or ears, and in some cases by nodular swelling on head, snout, cervical region, abdomen, ears and/or legs. These findings occurred shortly after dosing, were transient in nature, maximal between approximately 1 to 2 hours after dosing, disappearing thereafter. There was a large interindividual variation in this response, with no dose-response relationship. Mechanistic studies to clarify the cause for erythema were not indicative of a histamine-based mechanism of action.

In an oral 3 month dog toxicology study with compound III in beagle dog, slight to severe erythema of the skin, accompanied by swelling, was noted in the majority of the animals dosed at 120 mg/kg/day, throughout the entire treatment period. In some cases, these symptoms started as maculate erythema and/or nodular swelling and progressed to diffuse/general erythema and swelling. Signs were predominantly visible in areas with thin/sparse fur including the ears, periorbital region and abdomen. The findings were transient, with maximal severity about one hour after dosing and disappearing or decreasing to lower severity by 4 hours post-administration. After 5 weeks of treatment, one of four males dosed at 40 mg/kg/day exhibited general erythema. No erythema or edema was observed in any animals at the dose level of 10 mg/kg/day.

Compound II:

In a single dose escalation/5 day repeat dose dog toxicology study, beagle dogs were treated with compound II according to the current invention at dose levels from 40 up to 144 mg/kg day. No evidence of edema or erythema was observed in any of the animals in the study In a subsequent 1-month toxicology study with compound II at dose levels of 5, 20 and 40 mg/kg/day in beagle dogs, neither erythema nor edema was noted during the study period.

So oral administration of compound III produced erythema and edema in the beagle dog, as observed by clinical observations, in toxicology studies of up to 1 month in duration. Although the incidence of these findings appeared to increase with increasing duration of dosing and dose level, there was large inter-individual variation in the severity of the effect. In contrast, oral administration of compound II did not induce erythema and/or edema in the beagle dog in toxicology studies up to 1 month in duration.

Pharmacokinetics of Compound II and Boosting Effect of Ritonavir in Fed Male Beagle Dogs after Single Oral Administration of Compound II at 10 or 40 mg/kg.

The present study was performed to study the plasma pharmacokinetics of compound II in male beagle dogs after single oral administration doses of 10 and 40 mg/kg, and to evaluate the potential boosting effect of ritonavir, dosed at 10 mg/kg twice daily, on the bioavailability of compound II.

Beagle dogs (7-11 kg body weight) were dosed after feeding. Both compound II and ritonavir were given by gavage of an oral solution. All animals first received compound II alone, and after a washout of one week, the combination of ritonavir and compound II in the morning. Ritonavir dosing was repeated in the evening and on the next day's morning. Plasma was sampled to measure compound II and ritonavir concentrations until 32 hours after dosing of compound II.

The results of the study demonstrate that ritonavir is a potent pharmacokinetic enhancer for compound II in dogs. Both the total plasma exposure (AUC) and the peak plasma concentrations ($C_{max}$) of compound II markedly increased after co-administration with twice-daily dosing of 10 mg/kg ritonavir, as detailed in Table 4 and FIG. 1 representing the mean plasma concentration time plots for compound II with and without co-administration of ritonavir.

TABLE 4

Relative bioavailability ($F_{rel}$) of compound II at 10 and 40 mg/kg in beagle dogs, with and without co-administration of ritonavir

| | 10 mg/kg compound II | | | 40 mg/kg compound II | | |
|---|---|---|---|---|---|---|
| Treatment | without Ritonavir | with Ritonavir | Ratio or $F_{rel}$ (%) | without Ritonavir | with Ritonavir | Ratio or $F_{rel}$ (%) |
| $C_{max}$ (ng/ml) | 123 | 879 | 7.1 | 1194 | 4223 | 3.6 |
| $AUC_{0-inf}$ (h · ng/ml) | 330 | 4373 | 1378% | 2293 | 23625 | 1083% |

AUCs increased over 10-fold, whereas $C_{max}$ increased 4 to 7-fold. The latter indicates an improved absorption and decreased first-pass effect for compound II in the presence of ritonavir. The higher increase in AUC indicates that the primary ritonavir effect is in reducing the rate of elimination of compound II.

Film-Coated Tablets

Preparation of Tablet Core

A mixture of 100 g of active ingredient, in casu a compound of formula (I), 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenated. The tablet cores are coated with the thus obtained mixture in a coating apparatus.

The invention claimed is:

1. A compound having the formula (I)

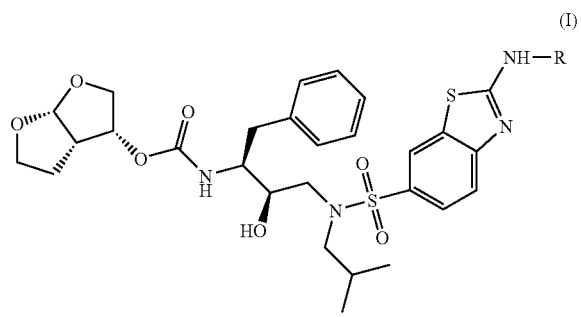

a salt, stereoisomeric form or stereoisomeric form thereof wherein

R is a piperidine ring substituted on the N-atom in the ring by $C_{3-7}$ cycloalkyl.

2. A compound according to claim 1 wherein $C_{3-7}$ cycloalkyl is $C_5$-cycloalkyl.

3. A compound according to claim 2 having the formula (II)

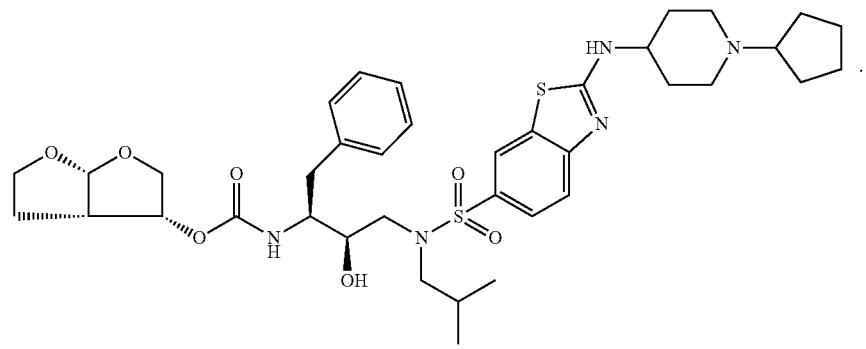

4. A pharmaceutical composition comprising an effective amount of at least one compound as claimed in claim 1 and a pharmaceutically tolerable excipient.

5. A composition comprising at least (a) a compound of formula (I) as claimed in claim 1 and, (b) a second antiretroviral agent for the simultaneous, separate or sequential use.

6. A composition according to claim 5 wherein the second agent is ritonavir.

7. A composition according to claim 6 wherein the compound of formula II is (1-benzyl-3-{[2-(1-cyclopentyl-piperidin-4-ylamino)-benzothiazole-6-sulfonyl]-isobutyl-amino}-2-hydroxy-propyl)-carbamic acid hexahydro-furo[2,3-b]furan-3-yl ester.

8. A method of inhibiting a protease of a multi-drug resistant retrovirus in a mammal infected with said retrovirus comprising administering a protease-inhibiting amount of a compound according to claim 1 to said mammal in need thereof.

9. A method of treating or combating infection or disease associated with multi-drug resistant retrovirus infection in a mammal comprising administering an effective amount of at least one compound according to claim 1 to said mammal.

10. A method of inhibiting multi-drug resistant retroviral replication comprising contacting a retrovirus with an effective amount of at least one compound according to claim 1.

* * * * *